(12) United States Patent
Hwang et al.

(10) Patent No.: US 10,607,145 B2
(45) Date of Patent: Mar. 31, 2020

(54) DETECTION ALGORITHMS FOR DISTRIBUTED EMISSION SOURCES OF ABNORMAL EVENTS

(71) Applicant: International Business Machines Corporation, Armonk, NY (US)

(72) Inventors: Youngdeok Hwang, Yorktown Heights, NY (US); Jayant R. Kalagnanam, Tarrytown, NY (US); Xiao Liu, Singapore (SG); Kyong Min Yeo, Scarsdale, NY (US)

(73) Assignee: International Business Machines Corporation, Armonk, NY (US)

( * ) Notice: Subject to any disclaimer, the term of this patent is extended or adjusted under 35 U.S.C. 154(b) by 1160 days.

(21) Appl. No.: 14/949,198

(22) Filed: Nov. 23, 2015

(65) Prior Publication Data

US 2017/0147927 A1    May 25, 2017

(51) Int. Cl.
*G06N 5/04*    (2006.01)
*G01N 33/00*   (2006.01)

(52) U.S. Cl.
CPC ......... *G06N 5/045* (2013.01); *G01N 33/0063* (2013.01)

(58) Field of Classification Search
CPC .... G01N 33/0063; G06N 5/045; G05B 23/02; G06F 17/30; A61B 5/00; H04L 29/06
See application file for complete search history.

(56) References Cited

U.S. PATENT DOCUMENTS

2005/0069207 A1*  3/2005 Zakrzewski ....... B64D 45/0015
                                                 382/190
2014/0332994 A1* 11/2014 Danes ................. G01N 23/223
                                                 264/40.1

OTHER PUBLICATIONS

'Design and Development of a Prototype System for Detecting Abnormal Weather Observations': Mateo, 2008, ACM, 978-1-60558-101.*
'Pollution level assessment and control of emission rates': Skiba, 2007, 2007 Nova Science Publishers, ISBN 978-1-60021-804.*
'Stochastic reconstruction of multiple source atmospheric contaminant dispersion events': Wade, 2013, Elsevier, Atmospheric Environment 74 (2013) 45e51.*
Yee, E. Inverse Dispersion of an Unknown Number of Contaminant Sources. 15th Joint Conference on the Applications of Air Pollution Meteorology with the A&WMA, 2008.
(Continued)

*Primary Examiner* — Li B. Zhen
*Assistant Examiner* — Peter Coughlan
(74) *Attorney, Agent, or Firm* — Ryan, Mason & Lewis, LLP (57) ABSTRACT

Methods, systems, and computer program products for detection of an arbitrarily-shaped source of an abnormal event via use of a hierarchical reconstruction method are provided herein. A computer-implemented method includes detecting an abnormal event based on analysis of sensor data, wherein said analysis of the sensor data comprises comparing the sensor data to a user-defined threshold; generating a query based on the detected abnormal event; processing the query against one or more given data repositories; executing an inverse model using an output generated in relation to said processing to identify a source of the detected abnormal event, wherein the source comprises an arbitrary shape; and outputting the identified source of the detected abnormal event.

18 Claims, 2 Drawing Sheets

(56) References Cited

OTHER PUBLICATIONS

Farmer et al. Source Identification from Line Integral Measurements and Simple Atmospheric Models, Inverse Problems and Imaging, vol. 7, No. 2, 2013, 471-490.
Singh et al. Inverse Modelling for Identification of Multiple-Point Releases from Atmospheric Concentration Measurements. Boundary-Layer Meteorol (2013) 146:277-295.
Ling, L. Point Sources Identification Problems for Heat Equation. Commun. Comput. Phys. May 2009, vol. 5, No. 5, pp. 897-913.
Keats et al. Bayesian inference for source determination with applications to a complex urban environment, Atmospheric Environment 41(2007) 465-479.
Lushi et al. An inverse Gaussian plume approach for estimating atmospheric pollutant emissions from multiple point sources, (2010).
Wade et al. Stochastic reconstruction of multiple source atmospheric contaminant dispersion events, Boise State University, ScholarWorks (2013).
Singh et al. A least-squares inversion technique for identification of a point release: Application to Fusion Trials 2007, Atmospheric Environment 92 (2014) 104-117.
Chai et al. Source term estimation using air concentration measurements and a Lagrangian dispersion model = Experiments with pseudo and real cesium-137 observations from the Fukushima nuclear accident, Atmospheric Environment 105 (2015) 241-251.

\* cited by examiner

DETECTION ALGORITHMS FOR DISTRIBUTED EMISSION SOURCES OF ABNORMAL EVENTS

FIELD

The present application generally relates to information technology, and, more particularly, to source determination techniques.

BACKGROUND

Air pollution can pose environmental risks to respiratory and cardiovascular health. Additionally, when instances of high air pollution are observed and/or noted, efficiently identifying the source of such air pollution can facilitate mitigation of possible public health hazards.

Event source detection can be utilized and/or implementing in connection with multiple contexts, including the example context noted above. However, existing source detection approaches commonly include using models that are limited to minimal number of point sources and/or require a large amount of data to function.

SUMMARY

In one embodiment of the present invention, techniques for the detection of distributed sources for an abnormal event via use of a hierarchical reconstruction method are provided. An exemplary computer-implemented method can include steps of detecting an abnormal event based on analysis of sensor data, wherein analysis of the sensor data includes comparing the sensor data to a user-defined threshold; generating a query based on the detected abnormal event; processing the query against one or more given data repositories; executing an inverse model using an output generated in relation to the processing step to identify a source of the detected abnormal event, wherein the source comprises an arbitrary shape; and outputting the identified source of the detected abnormal event.

Another embodiment of the invention or elements thereof can be implemented in the form of an article of manufacture tangibly embodying computer readable instructions which, when implemented, cause a computer to carry out a plurality of method steps, as described herein. Furthermore, another embodiment of the invention or elements thereof can be implemented in the form of an apparatus including a memory and at least one processor that is coupled to the memory and configured to perform noted method steps.

Yet further, another embodiment of the invention or elements thereof can be implemented in the form of means for carrying out the method steps described herein, or elements thereof; the means can include hardware module(s) or a combination of hardware and software modules, wherein the software modules are stored in a tangible computer-readable storage medium (or multiple such media).

These and other objects, features and advantages of the present invention will become apparent from the following detailed description of illustrative embodiments thereof, which is to be read in connection with the accompanying drawings.

DETAILED DESCRIPTION

As described herein, an embodiment of the present invention includes hierarchical reconstruction techniques for a distributed source of an abnormal event. As also detailed herein, at least one embodiment of the invention is described within the context of hierarchical pollution source reconstruction for an abnormal pollution event, but it should be noted that the techniques described herein can be carried out and/or implemented in connection with additional source reconstruction contexts.

By way of example, one or more embodiments of the invention can include identifying the source of air pollution from a limited number of data items. The amount of data items required to carry out such an embodiment of the invention can vary. By way merely of illustration, an example embodiment of the invention can include obtaining and/or utilizing the measurements from a sensor network at the detection time of an abnormal event.

Additionally, at least one embodiment of the invention can include utilizing an inverse model to estimate arbitrary spatial distribution of pollution sources responsible for a one-time measurement from a sensor network, wherein the sources can include single or multiple points or areas, or multiple disjoint areas. As noted above, such an inverse model can be implemented to determine the pollution source responsible for a particular one-time observation.

Accordingly, in contrast to disadvantageous existing approaches, at least one embodiment of the invention can include computing a pollution source estimation from a small and/or limited number of data items (such as a one-time snapshot and/or observation), as well as computing a pollution source estimation for an arbitrary shape of pollution emission distribution.

Figure 1:
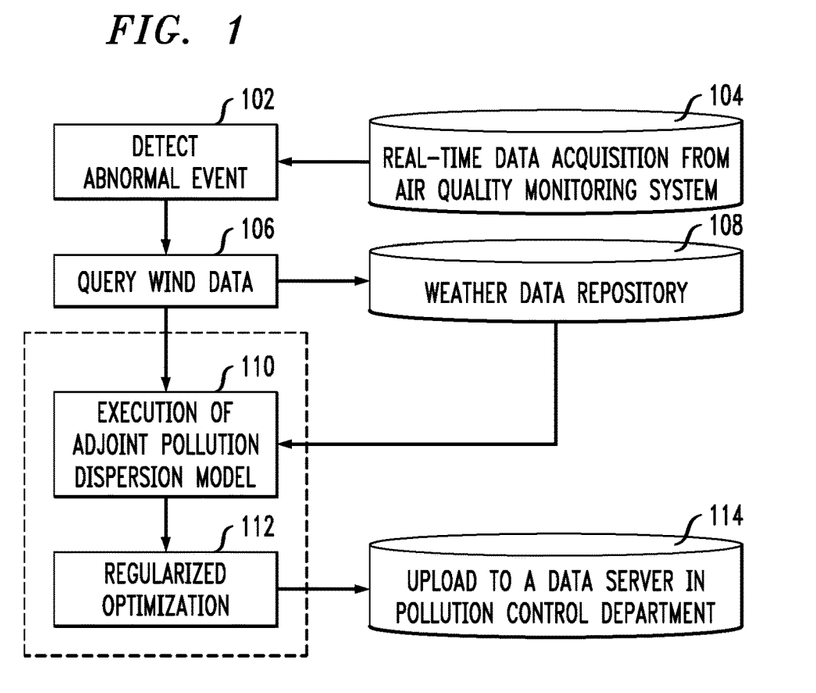
FIG. 1 is a diagram illustrating system architecture, according to an example embodiment of the invention.

FIG. 1 is a diagram illustrating system architecture, according to an example embodiment of the invention. By way of illustration, FIG. 1 depicts an abnormal event detection component 102, which receives input from a database or system 104 such as an air quality monitoring system, wherein the input can include real-time data acquired by system 104. As used herein, "real-time data" can include a continuous stream of sensor measurement being transmitted from a sensor network to a data server.

Additionally, an "abnormal event," as used herein, can include an instance wherein the (air) pollution measured via the sensor network is larger than a user-defined threshold. Continuing with the example of an air pollution source detection, a wind data query component 106 can generate a query, based on the event detected via component 102, and submit the query to a database 108 such as, for example, a weather data repository. As used herein, a "query" can include time-range information and can be sent to a weather data repository to retrieve the weather data and/or the meteorology information for the requested time range.

As also depicted in FIG. 1, the query component 106 and the database 108 provide related input to a model execution component 110. As noted, the query component 106 sends the time-range information to the weather data repository 108. The weather data repository 108 then sends the meteorological data for the requested time range to component 110. Further, the query component 106 also sends the time-range information to component 110 so that component 110 can decide and/or determine the computer model simulation period.

In accordance with the example embodiment detailed in connection with FIG. 1, component 110 can utilize the input provided by the query component 106 and the database 108 to execute an adjoint pollution dispersion model. By using the information from query component 106 and the data from the repository 108, the adjoint pollution dispersion model component 110 computes the possible pollution source locations for the pollution concentrations measured at each sensor. By way merely of illustration, consider the following example. If there are 30 sensors, the adjoint model provides 30 possible source locations (one source location for each sensor). The adjoint model can be based on computational physics equations, which can run automatically once the information from 106 and 108 are received.

The output from the execution of the model via component 110 is provided to an optimization component 112, wherein a hierarchical reconstruction method is employed to identify the pollution source locations and strengths. Subsequently, the identified pollution emission source via component 112 is provided to a database and/or server 114 in a pollution control department to trigger an alarm and/or to provide decision support.

Accordingly, the example embodiment detailed in connection with FIG. 1 includes a system for identifying the source of an air pollution event. As noted above, such a system includes implementing an inverse model (such as an adjoint pollution dispersion model) to estimate pollution sources using the spatial distribution of pollution emission sources for a snapshot event, wherein the sources can include points, an area, or multiple disjoint areas. In one or more embodiments of the invention, the model can be designed to identify pollution sources responsible for a particular event.

Further, at least one embodiment of the invention includes developing a hierarchical source reconstruction method as a regularized optimization problem, which is used to identify the pollution source via component 112. The hierarchical reconstruction is achieved by modeling the computational mesh system for the possible source locations by uniform random variables. By representing the uncertainty in the computational mesh system as random variables and modeling the random variables by using a generalized polynomial chaos expansion, in the hierarchical source reconstruction, (i) the number of unknown parameters in the optimization formulation can be reduced dramatically and (ii) the sparsity of the solution (arbitrary spatial distribution of the source) can be naturally explored by a (new) regularization model, which can impose the fused LASSO regularization on the expectation of the solution and the ridge regularization on the variance of the solution.

Accordingly, as detailed in connection with FIG. 1, one or more embodiments of the invention include implementing shrinkage estimators based on the hierarchical structure of a parameter, as well as carrying out a low-dimensional approximation supplemented with a stochastic modeling. In such an embodiment, the low-dimensional approximation can include a pollution dispersion equation as follows:

$$\frac{\partial}{\partial t}\emptyset(x,t) = -\nabla \cdot (u\emptyset) + \nabla \cdot (K \cdot \nabla \emptyset) + Q(x).$$

Here, $\emptyset(x,t)$ represents pollution concentration at location x at time t, u represents a wind value, and K is a diffusion coefficient. Based on such an equation, determining $Q(x)$ can include an infinite dimensional optimization problem. Accordingly, a low-dimensional approximation of $Q(x)$ can include the following: $Q(x) \cong \sum_{i=1}^{N_s} \beta_i \mathcal{P}_i(x)$, in which $$\mathcal{P}_i(x) = \frac{1}{2\pi(c\Delta)^2} \exp\left[-\frac{1}{2}\frac{|x-y_i|^2}{(c\Delta)^2}\right].$$

Here, $y_i$ represents the center of the i-th kernel $\mathcal{P}_i$, and c represents a tuning parameter.

Additionally, at least one embodiment of the invention can include determining a set of parameters, $\beta_i$, as follows:

$$\frac{\partial}{\partial t}\emptyset(x,t) + \nabla \cdot (u\emptyset) - \nabla \cdot (K \cdot \nabla \emptyset) = \sum_{i=1}^{N_s} \beta_i \mathcal{P}_i(x),$$

subjected to a constraint such as: $\Phi_i(t^0) = \langle \emptyset(x,t), x(x,t; x_i^0, t^0) \rangle + \epsilon$ for $i=1, \ldots, N_0$ for the sensor measurement $\Phi$ at the time of observation $t^0$ and at the sensor location $x_i^0$, computer simulation of pollution concentration $\emptyset$, and the sensor-detection function x. The angle brackets denote an inner product between two functions, such that $\langle a(x,t), b(x,t) \rangle = \int_{x \in \mathbb{R}^3} \int_{-\infty}^0 a(x,t+\tau) b(x,t+\tau) \, d\tau dx$, for any arbitrary functions $a(x,t)$ and $b(x,t)$.

As described herein, one or more embodiments of the invention also include adjoint modeling. Using an adjoint model, the number of computations can be reduced from the number of parameters O(100~1,000) to the number of observation stations O(10). By way of example, at least one embodiment of the invention includes implementing the following adjoint dispersion model:

$$\mathcal{D}^* \emptyset_i^* = -\frac{\partial}{\partial t}\emptyset_i^* - u \cdot \nabla \emptyset_i^* - \nabla \cdot (K \cdot \nabla \emptyset_i^*) = x_i$$

for every observation station x, which provides the following: $\langle \emptyset, x_i \rangle = \langle \emptyset^*_i, Q \rangle = \sum_{j=1}^{N_s} \langle \emptyset^*_i, \mathcal{P}_j \rangle \beta_j$, in which $\emptyset^*_i$ represents a conjugate concentration field. Subsequently, the adjoint solution can be related with an actual observation by the following: $\Phi = X\beta + \epsilon$, $X_{ij} = \langle \emptyset^*_i, \mathcal{P}_j \rangle$.

Additionally, as also noted above, one or more embodiments of the invention can include implementing stochastic modeling. Such modeling can depend, for example, on the choice of the center of the kernels, $y_i$. Such a choice may not correctly represent the distribution between collocation points, defined by the collection of the kernel center points $y_i$s, and results can be changed when the collocation set changes (representing model uncertainty). In representing model uncertainty, at least one embodiment of the invention includes defining the set of collocation points as follows:

$$\mathcal{W} = s_1 \otimes s_2,$$

$$s_1 = \{x_1^i; x_1^i = x_1^0 + (i-1) \times \Delta x_1, i-1, \ldots, N_x\},$$

$$s_2 = \{x_2^i; x_2^i = x_2^0 + (i-1) + \Delta x_2, i-1, \ldots, N_y\}.$$

Here, the collocation set $\mathcal{W}$ is defined by a tensor product of two one-dimensional sets, $s_1$ and $s_2$, in which $x_i^0$ represents the starting point in the i-th direction, $\Delta x_i$ represents the interval between the neighboring points, and $N_i$ represents the number of the points.

Further, one or more embodiments of the invention include representing the collocation set as a stochastic variable, as follows: $\mathcal{W}^*(\xi_1,\xi_2)=(s_1+\xi_1\Delta x_1)\otimes(s_2+\xi_2\Delta x_2)$, in which $\xi_1$ and $\xi_2$ are random variables with uniform distribution in the interval (−0.5, 0.5). Also, the random variables are selected as uniform random variables such that $W^*$ covers the entire domain uniformly. Also, because the collocation set is a stochastic variable, both the basis functions and the parameters become stochastic variables as follows: $Q(x;\xi)=\Sigma_{i=1}^{N_s}\mathcal{P}_i(x;\xi)\beta_i(\xi)$, and thus: $X_{ij}(\xi)=\langle \phi^*_i, \mathcal{P}_j(\xi) \rangle$. Using the random variables, the problem of finding the deterministic source $Q(x)$ can be changed to a stochastic problem of finding a random function, $Q(x;\xi)$. The two equations describe that both $Q$ and $X_{ij}$ are stochastic functions and are defined as detailed herein.

With the uncertainty modeling detailed above, in at least one embodiment of the invention, the source estimation problem becomes the following: $\min \frac{1}{2}\|\Phi-E[X(\xi)\beta(\xi)]\|_2^2 + \mathcal{R}(\beta)$, in which $E[X(\xi)\beta(\xi)] = \int X(\xi)\beta(\xi)p(\xi)d\xi$ for the probability density functions for $\xi$, $p(\xi)$. Additionally, the stochastic variables can be represented by orthogonal hierarchical polynomials, $\Psi_l(\xi)$, as follows:

$$X_{ij}(\xi)=\Sigma_{k=0}^{\infty}\hat{X}_{ij}^k\Psi_k(\xi)=\langle \phi^*_i, \Sigma_k \hat{\mathcal{P}}^k(x)\Psi_k(\xi) \rangle,$$

$$\beta(\xi)=\Sigma_{l=0}^{\infty}\hat{\beta}^l\Psi_l(\xi),$$

in which $\hat{X}_{ij}^k$, $\hat{\mathcal{P}}_j^k$ and $\hat{\beta}^l$ denote the modal coefficients of $\Psi_l(\xi)$ for $X_{ij}$, $\mathcal{P}_j(x;\xi)$, and $\beta(\xi)$, respectively. Accordingly, $$E[X_{ij}(\xi)\beta_j(\xi)] = \sum_{k=0}^{M} \langle \phi^*_i, \hat{\mathcal{P}}_j^k(x) \rangle \hat{\beta}_j^k, \text{ and}$$

$$\hat{\mathcal{P}}_j^k(x) = \frac{l}{2\pi(c\Delta)^2}\int \exp\left[-\frac{1}{2}\frac{|x-y_j-\xi\delta x|^2}{(c\Delta)^2}\right]\Psi_k(\xi)p(\xi)d\xi.$$

Here, as the random variables are chosen to have uniform distributions, the orthogonal polynomial, $\Psi_l(\xi)$, is the Legendre polynomial.

At least one embodiment of the invention can also include implementing hierarchical reconstruction techniques. In such an embodiment, due to the convolution of the basis function in the physical space (for example, a Gaussian distribution) and the orthogonal polynomial in the random space (for example, a Legendre polynomial), the resulting optimization problem can be represented by a hierarchical reconstruction.

Additionally, as detailed herein as well as in connection with FIG. 1, one or more embodiments of the invention include implementing regularization optimization for hierarchical reconstruction. By way of illustration, consider the following example wherein the number of data items is the number of air quality monitoring stations: O(10). Also, in this example, the number of unknown parameters is the number of collocation points multiplied by the number of modes: O(10,000). Regularization, based on the sparsity in the hierarchical structure, can be implemented as follows:

$$\underset{\hat{\beta}\in\mathbb{R}^{N_s\times M}}{\operatorname{argmin}} \frac{1}{2}\left\|\Phi-\sum_{k=0}^{M}\hat{X}^k\hat{\beta}^k\right\|_2^2 + \lambda_1\|D\hat{\beta}^0\|_1 + \lambda_2\sum_{k=1}^{M}\|\hat{\beta}^k\|_2^2,$$

such that $\min(\Sigma_{k=0}^M \Sigma_{j=1}^{N_s} \hat{\mathcal{P}}_j^k(x)\hat{\beta}_j^k) \geq 0$. Here, M represents the number of the polynomial modes, D represents a matrix of the indices about the spatial graph of the $\beta_j$s, $\lambda_1$ and $\lambda_2$ represent tuning parameters, and and $\|\ \|_1$ and $\|\ \|_2^2$, respectively, denote the 1-1 and 1-2 norms.

One or more embodiments of the invention can also include implementing a spatial smoothness condition with a shrinkage estimator. The smoothness condition is imposed by a fused least absolute shrinkage and selection operator (LASSO) through the connectivity matrix D with the shrinkage operator, $\|\ \|_1$. For example, the fused LASSO can be constructed as $\|D\hat{\beta}^0\|_1 = \Sigma_{(i,j)}|\hat{\beta}_i^0 - \hat{\beta}_j^0|$, for every neighboring pairs (i, j). Also, at least one embodiment of the invention can include implementing an uncertainty minimization estimator in connection with the uncertainty of the model parameter as follows: $\text{Var}(\beta_j)=\Sigma_{k=1}^M\|\hat{\beta}^k\|_2^2$.

Figure 2:
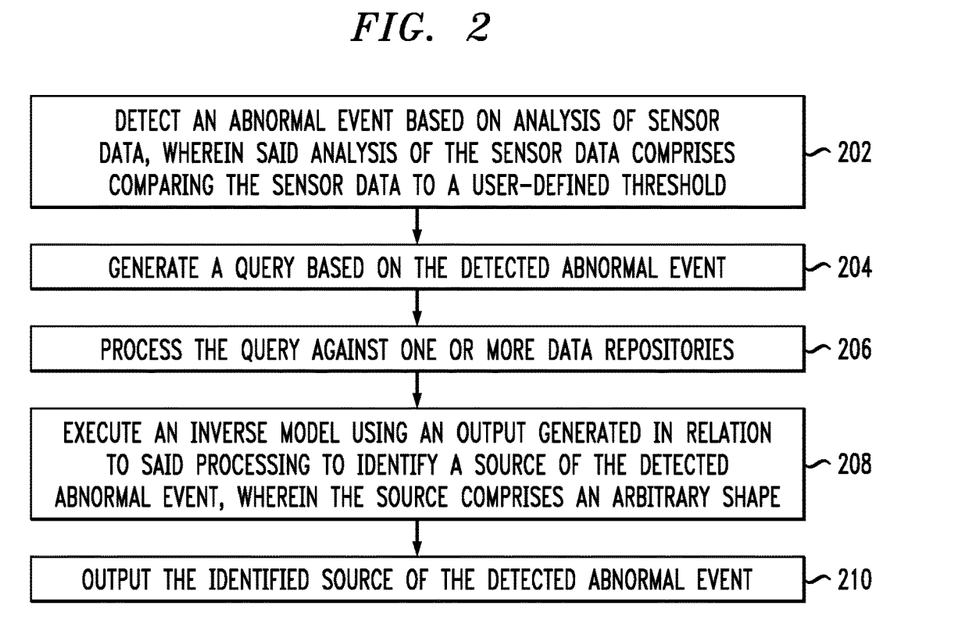
FIG. 2 is a flow diagram illustrating techniques according to an embodiment of the invention.

FIG. 2 is a flow diagram illustrating techniques according to an embodiment of the present invention. Step 202 includes detecting an abnormal event based on analysis of sensor data, wherein said analysis of the sensor data comprises comparing the sensor data to a user-defined threshold. The abnormal event can include an abnormal air pollution event. Also, the sensor data can include a one-time observation. Further, the sensor data can include real-time air quality data.

Step 204 includes generating a query based on the detected abnormal event. Step 206 includes processing the query against one or more data repositories (such as, for example, one or more weather data repositories).

Step 208 includes executing an inverse model using an output generated in relation to said processing to identify a source of the detected abnormal event, wherein the source comprises an arbitrary shape. The inverse model can include a dispersion model. Additionally, executing the inverse model can include implementing a hierarchical reconstruction technique. Further, an uncertainty factor associated with the inverse model can be modeled by one or more uniform random variables.

The source of the detected abnormal event can include a single item. The source of the detected abnormal event comprises a distribution across multiple items, wherein the distribution can include an arbitrary distribution shape. Also, the distribution across multiple items can include a distribution across multiple disjoint items.

Additionally, the source of the detected abnormal event can include a single geographic area. The source of the detected abnormal event can also include a distribution across multiple geographic areas, wherein the distribution can include an arbitrary distribution shape. Further, the distribution across multiple geographic areas can include a distribution across multiple disjoint geographic areas.

Step 210 includes outputting the identified source of the detected abnormal event. Outputting the identified source can include uploading the identified source of the detected abnormal event to a server.

In accordance with one or more embodiments of the invention, the techniques depicted in FIG. 2 can also include applying one or more regularized optimizations to the identified source of the detected abnormal event.

The techniques depicted in FIG. 2 can also, as described herein, include providing a system, wherein the system includes distinct software modules, each of the distinct software modules being embodied on a tangible computer-readable recordable storage medium. All of the modules (or any subset thereof) can be on the same medium, or each can be on a different medium, for example. The modules can include any or all of the components shown in the figures and/or described herein. In an embodiment of the invention, the modules can run, for example, on a hardware processor. The method steps can then be carried out using the distinct software modules of the system, as described above, executing on a hardware processor. Further, a computer program product can include a tangible computer-readable recordable storage medium with code adapted to be executed to carry out at least one method step described herein, including the provision of the system with the distinct software modules.

Additionally, the techniques depicted in FIG. 2 can be implemented via a computer program product that can include computer useable program code that is stored in a computer readable storage medium in a data processing system, and wherein the computer useable program code was downloaded over a network from a remote data processing system. Also, in an embodiment of the invention, the computer program product can include computer useable program code that is stored in a computer readable storage medium in a server data processing system, and wherein the computer useable program code is downloaded over a network to a remote data processing system for use in a computer readable storage medium with the remote system.

An embodiment of the invention or elements thereof can be implemented in the form of an apparatus including a memory and at least one processor that is coupled to the memory and configured to perform exemplary method steps.

Figure 3:
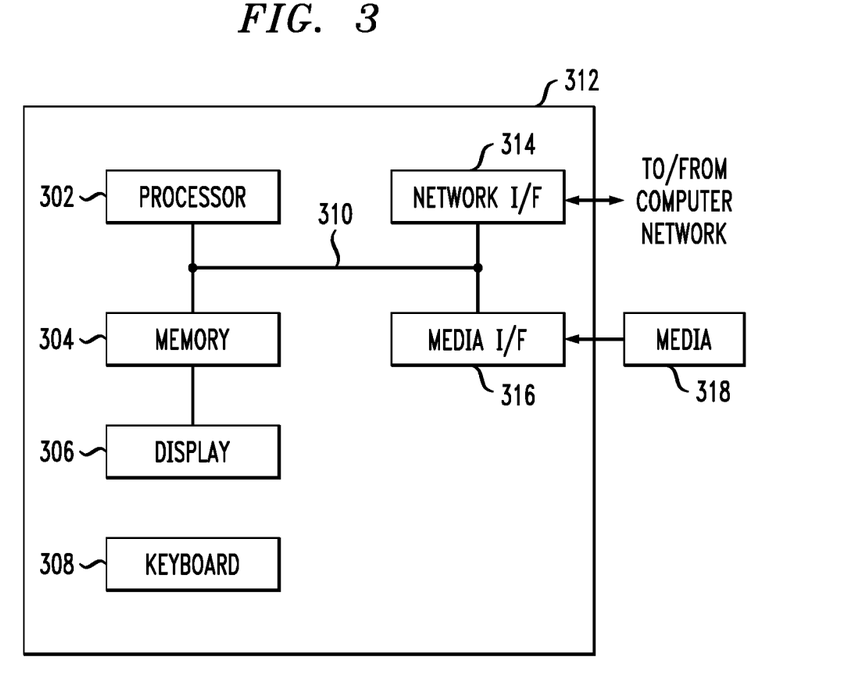
FIG. 3 is a system diagram of an exemplary computer system on which at least one embodiment of the invention can be implemented.

Additionally, an embodiment of the present invention can make use of software running on a computer or workstation. With reference to FIG. 3, such an implementation might employ, for example, a processor 302, a memory 304, and an input/output interface formed, for example, by a display 306 and a keyboard 308. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory), ROM (read only memory), a fixed memory device (for example, hard drive), a removable memory device (for example, diskette), a flash memory and the like. In addition, the phrase "input/output interface" as used herein, is intended to include, for example, a mechanism for inputting data to the processing unit (for example, mouse), and a mechanism for providing results associated with the processing unit (for example, printer). The processor 302, memory 304, and input/output interface such as display 306 and keyboard 308 can be interconnected, for example, via bus 310 as part of a data processing unit 312. Suitable interconnections, for example via bus 310, can also be provided to a network interface 314, such as a network card, which can be provided to interface with a computer network, and to a media interface 316, such as a diskette or CD-ROM drive, which can be provided to interface with media 318.

Accordingly, computer software including instructions or code for performing the methodologies of the invention, as described herein, may be stored in associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 302 coupled directly or indirectly to memory elements 304 through a system bus 310. The memory elements can include local memory employed during actual implementation of the program code, bulk storage, and cache memories which provide temporary storage of at least some program code in order to reduce the number of times code must be retrieved from bulk storage during implementation.

Input/output or I/O devices (including, but not limited to, keyboards 308, displays 306, pointing devices, and the like) can be coupled to the system either directly (such as via bus 310) or through intervening I/O controllers (omitted for clarity).

Network adapters such as network interface 314 may also be coupled to the system to enable the data processing system to become coupled to other data processing systems or remote printers or storage devices through intervening private or public networks. Modems, cable modems and Ethernet cards are just a few of the currently available types of network adapters.

As used herein, including the claims, a "server" includes a physical data processing system (for example, system 312 as shown in FIG. 3) running a server program. It will be understood that such a physical server may or may not include a display and keyboard.

The present invention may be a system, a method, and/or a computer program product at any possible technical detail level of integration. The computer program product may include a computer readable storage medium (or media) having computer readable program instructions thereon for causing a processor to carry out embodiments of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform embodiments of the present invention.

Embodiments of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It should be noted that any of the methods described herein can include an additional step of providing a system comprising distinct software modules embodied on a computer readable storage medium; the modules can include, for example, any or all of the components detailed herein. The method steps can then be carried out using the distinct software modules and/or sub-modules of the system, as described above, executing on a hardware processor 302. Further, a computer program product can include a computer-readable storage medium with code adapted to be implemented to carry out at least one method step described herein, including the provision of the system with the distinct software modules.

In any case, it should be understood that the components illustrated herein may be implemented in various forms of hardware, software, or combinations thereof, for example, application specific integrated circuit(s) (ASICS), functional circuitry, an appropriately programmed digital computer with associated memory, and the like. Given the teachings of the invention provided herein, one of ordinary skill in the related art will be able to contemplate other implementations of the components of the invention.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of another feature, step, operation, element, component, and/or group thereof.

At least one embodiment of the present invention may provide a beneficial effect such as, for example, pollution source estimation for an arbitrary shape of pollution emission distribution.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method, comprising:
detecting an abnormal event based on analysis of sensor data derived from a sensor network, wherein said analysis of the sensor data comprises comparing the sensor data to a user-defined threshold, and wherein the detected abnormal event comprises air pollution, measured via the sensor network, that exceeds the user-defined threshold;
generating a query based on the detected abnormal event;
processing the query against one or more data repositories;
executing an inverse model using an output generated in relation to said processing to identify a source of the detected abnormal event, wherein the source comprises an arbitrary shape, and wherein said executing the inverse model comprises implementing a hierarchical reconstruction technique by modeling a computational mesh system for possible sources of the detected abnormal event via uniform random variables, wherein modeling the computational mesh system comprises:
representing uncertainty in the computational mesh system as one or more uniform random variables; and
modeling the one or more uniform random variables by implementing a generalized polynomial chaos expansion in the hierarchical reconstruction technique;
and wherein said executing the inverse model further comprises implementing a least absolute shrinkage and selection operator; and
outputting the identified source of the detected abnormal event;
wherein the method is carried out by at least one computing device.

2. The computer-implemented method of claim 1, further comprising:
applying one or more regularized optimizations to the identified source of the detected abnormal event.

3. The computer-implemented method of claim 1, wherein the abnormal event comprises an abnormal air pollution event.

4. The computer-implemented method of claim 1, wherein the sensor data comprises a one-time observation.

5. The computer-implemented method of claim 1, wherein said sensor data comprises real-time air quality data.

6. The computer-implemented method of claim 1, wherein the inverse model comprises a dispersion model.

7. The computer-implemented method of claim 1, wherein the source of the detected abnormal event comprises a single item.

8. The computer-implemented method of claim 1, wherein the source of the detected abnormal event comprises a distribution across multiple items.

9. The computer-implemented method of claim 8, wherein the distribution across multiple items comprises an arbitrary distribution shape.

10. The computer-implemented method of claim 8, wherein the distribution across multiple items comprises a distribution across multiple disjoint items.

11. The computer-implemented method of claim 1, wherein the source of the detected abnormal event comprises a single geographic area.

12. The computer-implemented method of claim 1, wherein the source of the detected abnormal event comprises a distribution across multiple geographic areas.

13. The computer-implemented method of claim 12, wherein the distribution across multiple geographic areas comprises an arbitrary distribution shape.

14. The computer-implemented method of claim 12, wherein the distribution across multiple geographic areas comprises a distribution across multiple disjoint geographic areas.

15. The computer-implemented method of claim 1, wherein said outputting comprises uploading the identified source of the detected abnormal event to a server.

16. A computer program product, the computer program product comprising a computer readable storage medium having program instructions embodied therewith, the program instructions executable by a device to cause the device to:
detect an abnormal event based on analysis of sensor data derived from a sensor network, wherein said analysis of the sensor data comprises comparing the sensor data to a user-defined threshold, and wherein the detected abnormal event comprises air pollution, measured via the sensor network, that exceeds the user-defined threshold;
generate a query based on the detected abnormal event;
process the query against one or more given data repositories;
execute an inverse model using an output generated in relation to said processing to identify a source of the detected abnormal event, wherein the source comprises an arbitrary shape, and wherein said executing the inverse model comprises implementing a hierarchical reconstruction technique by modeling a computational mesh system for possible sources of the detected abnormal event via uniform random variables, wherein modeling the computational mesh system comprises:
representing uncertainty in the computational mesh system as one or more uniform random variables; and
modeling the one or more uniform random variables by implementing a generalized polynomial chaos expansion in the hierarchical reconstruction technique;
and wherein said executing the inverse model further comprises implementing a least absolute shrinkage and selection operator; and
output the identified source of the detected abnormal event.

17. The computer program product of claim 16, wherein the program instructions executable by a device further cause the device to:
apply one or more regularized optimizations to the identified source of the detected abnormal event.

18. A system comprising:
a memory; and
at least one processor coupled to the memory and configured for:
detecting an abnormal event based on analysis of sensor data derived from a sensor network, wherein said analysis of the sensor data comprises comparing the sensor data to a user-defined threshold, and wherein the detected abnormal event comprises air pollution, measured via the sensor network, that exceeds the user-defined threshold;
generating a query based on the detected abnormal event;

processing the query against one or more given data repositories;

executing an inverse model using an output generated in relation to said processing to identify a source of the detected abnormal event, wherein the source comprises an arbitrary shape, and wherein said executing the inverse model comprises implementing a hierarchical reconstruction technique by modeling a computational mesh system for possible sources of the detected abnormal event via uniform random variables, wherein modeling the computational mesh system comprises:

representing uncertainty in the computational mesh system as one or more uniform random variables; and modeling the one or more uniform random variables by implementing a generalized polynomial chaos expansion in the hierarchical reconstruction technique;

and wherein said executing the inverse model further comprises implementing a least absolute shrinkage and selection operator; and outputting the identified source of the detected abnormal event.

* * * * *